(12) United States Patent
Kawabata et al.

(10) Patent No.: US 8,323,620 B2
(45) Date of Patent: Dec. 4, 2012

(54) ULTRASOUND CONTRAST AGENT

(75) Inventors: Kenichi Kawabata, Kodaira (JP); Nami Sugita, Ranzan (JP); Shin-ichiro Umemura, Muko (JP)

(73) Assignee: Hitachi Medical Corporation, Tokyo (JP)

( * ) Notice: Subject to any disclaimer, the term of this patent is extended or adjusted under 35 U.S.C. 154(b) by 890 days.

(21) Appl. No.: 11/658,591

(22) PCT Filed: Aug. 4, 2005

(86) PCT No.: PCT/JP2005/014302
§ 371 (c)(1),
(2), (4) Date: Jan. 26, 2007

(87) PCT Pub. No.: WO2006/043359
PCT Pub. Date: Apr. 27, 2006

(65) Prior Publication Data
US 2008/0311046 A1   Dec. 18, 2008

(30) Foreign Application Priority Data

Oct. 22, 2004  (JP) ................................ 2004-307578

(51) Int. Cl.
*A61B 8/00*   (2006.01)
(52) U.S. Cl. ....................................... 424/9.5; 424/9.52
(58) Field of Classification Search .................. None
See application file for complete search history.

(56) References Cited

U.S. PATENT DOCUMENTS

| | | | |
|---|---|---|---|
| 5,536,489 A * | 7/1996 | Lohrmann et al. | 424/9.52 |
| 5,716,597 A | 2/1998 | Lohrmann et al. | |
| 6,083,484 A * | 7/2000 | Lohrmann et al. | 424/9.52 |
| 6,521,211 B1 | 2/2003 | Unger et al. | |

FOREIGN PATENT DOCUMENTS

WO   WO9421301   * 9/1994

OTHER PUBLICATIONS

International Search Report of PCT/JP2005/014302 mailed Oct. 25, 2005.
Theresa M. Allen, "Ligand-Targeted Therapeutics in Anticancer Therapy", Reviews, Nature Publishing Group, Oct. 2002, vol. 2, pp. 750-763.
Dilantha B. Ellegala, M.D., et al., "Imaging Tumor Angiogenesis With Contrast Ultrasound and Microbubbles Targeted to $\alpha_v\beta_3$", Circulation, Jul. 22, 2003, pp. 336-341.
Gregory M. Lanza et al., "A Novel Site-Targeted Ultrasonic Contrast Agent with Board Biomedical Application", Circulation, 1996, 15 pages.
S. Umemura et al., "Enhancement of Ultrasonic Absorption by Microbubbles for Therapeutic Application", 2001 IEEE Ultrasonics Symposium, pp. 1311-1314.
Thomas F. Miller et al., "Effects of perfluorochemical distribution and elimination dynamics on cardiopulmonary function", J Appl Physiol, vol. 90, 2001, pp. 839-849.

* cited by examiner

*Primary Examiner* — Michael G Hartley
*Assistant Examiner* — Jennifer Lamberski
(74) *Attorney, Agent, or Firm* — Stites & Harbison, PLLC; Juan Carlos A. Marquez, Esq

(57) ABSTRACT

An ultrasound contrast agent composed of at least one kind of low-boiling water-insoluble substance (with a boiling point lower than 37° C.) and at least one kind of high-boiling water-insoluble substance (with a boiling point higher than 37° C.). The former vaporizes to absorb ultrasonic energy upon application of ultrasound, thereby causing the latter to vaporize secondarily, with the resulting bubbles producing an echo image. It is less liable to bumping and hence safe.

10 Claims, 5 Drawing Sheets

FIG.1
(a) SYSTEM OF SINGLE SUBSTANCE
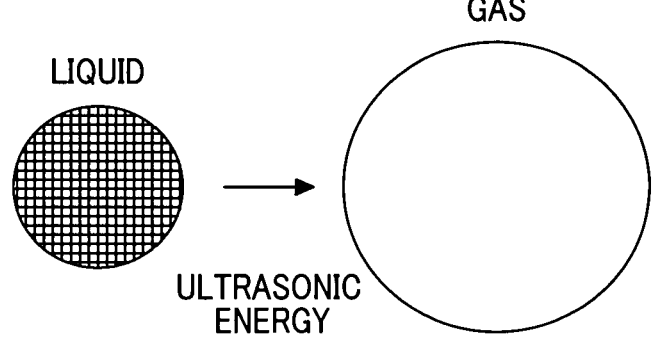
(b) SYSTEM OF MIXTURE
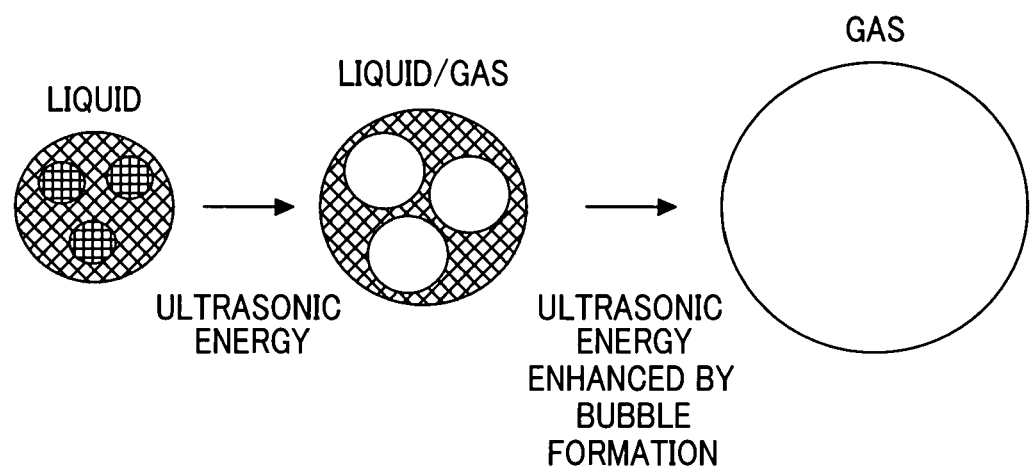

FIG.2

| LOW-BOILING WATER-INSOLUBLE SUBSTANCE | B.P., °C |
|---|---|
| DECAFLUOROBUTANE | 4 |
| 2-CHLORO-1, 1, 1-TRIFLUOROETHANE | 6.9 |
| NEOPENTANE | 9.5 |
| 1-CHLORO-1, 1, 2, 2-TETRAFLUOROETHANE | 10.2 |
| HEPTAFLUOROPROPYL BROMIDE | 12 |
| CYCLOBUTANE | 12 |
| 2H-PERFLUORO-t-BUTANE | 13 |
| FLUOROTRICHLOROMETHANE | 24 |
| DIBROMODIFLUOROMETHANE | 25 |
| 2-BROMO-1, 1, 1-TRIFLUOROETHANE | 26 |
| 2-METHYLBUTANE | 27.8 |
| PERFLUOROPENTANE | 29.5 |
| 1-PENTENE | 30 |
| PENTANE | 36 |

FIG.3

| HIGH-BOILING WATER-INSOLUBLE SUBSTANCE | B.P., °C |
|---|---|
| 2H, 3H-PERFLUOROPENTANE | 53.6 |
| PERFLUOROHEXANE | 56.6 |
| HEXANE | 69 |
| 1H-PERFLUOROHEXANE | 70 |
| PERFLUOROHEPTANE | 82.5 |
| HEPTANE | 98.3 |
| PERFLUOROOCTANE | 105 |

ULTRASOUND CONTRAST AGENT

TECHNICAL FIELD

The present invention relates to an ultrasound contrast agent for the ultrasonic diagnostic equipment and to a method for ultrasonography with said ultrasound contrast agent.

BACKGROUND ART

It is a long time since image diagnosis with X-ray CT, MRI (magnetic resonance imaging), ultrasonography, etc. became an essential tool in medical practice. These technologies produce images due to CT values, spin relaxation time, acoustic impedance, etc. varying from one living tissue to another. Imaging by them is called "anatomical imaging" because their physical values depend solely on the anatomic properties of the living body. By contrast, there is another type of imaging called "functional imaging", which is designed to examine tissues which are identical in structure but different in function. It is sometimes called "molecular imaging" when it is used to elucidate the structure of molecules (such as proteins) constituting a living body.

Molecular imaging is one of the research areas most attracting attention because of its potential application to elucidation of life phenomenon (such as development and differentiation) and diagnosis and therapy of diseases. Molecular imaging usually employs a "molecular probe" which is a substance with structural selectivity for molecules constituting a living body. It is given something that visualizes its distribution in a living body. An example of a molecular probe to target a tumor is disclosed in Non-Patent Document 1. Major molecular probes are peptides and proteins such as antibodies.

A molecular probe in a living body is visualized on the image diagnostic equipment when it chemically or physically combines with a substance called contrast agent or reporter that modifies its structure. The term "contrast agent" usually denotes a substance used to diagnose the blood flow. It is generally used in ultrasonography. A prevailing ultrasound contrast agent is minute bubbles with a diameter of the order of micrometers. Ultrasonography visualizes substances that vary in acoustic impedance (product of density and sound velocity) from one place to another. It easily visualizes air bubbles in a living body which have a much smaller acoustic impedance than tissues constituting a living body (ca. $0.004 \times 10^6$ kg/m$^2$·s vs. ca. $1.5 \times 10^6$ kg/m$^2$·s). Moreover, it selectively visualizes signals from minute air bubbles of the order of micrometers which resonate with diagnostic ultrasound of high-frequencies in the MHz band and generate higher harmonics from the impingent ultrasound. This leads to highly sensitive imaging.

One conceivable way of realizing molecular imaging with ultrasound is to employ an ultrasound contrast agent composed of bubbles and molecular probes which is in use for diagnosis of blood flow as mentioned above. In fact, such a ultrasound contrast agent responsive to thrombi has been developed, as disclosed in Patent Document 1. Another type of ultrasound contrast agent responsive to new blood vessel is also under study, as disclosed in Non-Patent Document 2. As disclosed in Non-Patent Document 3, it is a liquid differing in acoustic impedance from a living body which is enclosed in microcapsules of submicron size capable of migrating from blood vessels into tissues.

Another ultrasound contrast agent having all the merits of earlier ones is disclosed in Patent Document 2. It is a liquid compound in the form of fine particles divided by a surfactant, which is vaporized by ultrasound in a living body after administration. This type of ultrasound contrast agent will permit highly sensitive imaging by resonance because it is not limited in retention time in a living body and parts to which it is applied and because it keeps a gas phase during imaging operation.

Patent Document 1:
  U.S. Pat. No. 6,521,211
Patent Document 2:
  U.S. Pat. No. 5,716,597
Non-Patent Document 1:
  Allen, Nature Rev. Cancer, 2, 750-763 (2002)
Non-Patent Document 2:
  Ellegala et al., Circulation, 108, 336-341 (2003)
Non-Patent Document 3:
  Lanza et al., Circulation, 94, 3334-3340 (1996)
Non-Patent Document 4:
  Umemura et al., Prc. IEEE Ultrasonics Symposium, 2, 1311-1314 (2001)

DISCLOSURE OF THE INVENTION

Problems for Solution by the Invention

The conventional ultrasound contrast agent in the form of micron-size microbubbles is applicable only to vascular ultrasonography. In addition, it is easily broken even by ultrasound at a low level of intensity for diagnosis and hence it does not allow for continuous imaging once it has been used for imaging. Moreover, being in the form of bubbles (gas), it is discharged from a living body by gas exchange in the lungs and hence its residence time in the blood vessel is only ten-odd minutes.

The ultrasound contrast agent according to Non-Patent Document 3 seems applicable to any other parts than blood vessels and capable of residing longer in blood vessels. However, being in the form of liquid droplets, it does not produce resonance unlike the ultrasound contrast agent in the form of microbubbles and hence it is poor in sensitivity.

Application of ultrasound to a liquid containing bubbles as mentioned in Non-Patent Document 4 makes bubbles absorb a large portion of ultrasonic energy, resulting in a temperature rise in the vicinity of bubbles, because absorbed energy converts into heat.

Meanwhile, low-invasive heat therapy (such as ultrasonic coagulation and RF heating) needs a means for monitoring the temperature of lesions in real time. Unfortunately, only MRI (which is large medical equipment) is a low-invasive temperature monitoring means that is available at present, but it is not readily applicable in practice. There is a need for a simple one that will supersede MRI.

There are three conceivable types of ultrasound contrast agent to be used in conjunction with the molecular probe for ultrasonic molecular imaging. They include microbubbles, encapsulated liquid (to be used as such), and encapsulated liquid (to be used after evaporation by ultrasound). The third is considered best from the standpoint of applicability, residence time, and sensitivity.

The above-mentioned ultrasound contrast agent in the form encapsulated liquid, which is evaporated by application of ultrasound after administration, is an emulsion of a substance having a boiling point lower than 37° C. which is dispersed into a medium with the help of a surfactant such as lecithin. Unfortunately, the substance stabilized in an emulsion takes on the shape of droplets with a diameter larger than 1 µm. Such droplets are so large that their use is limited to blood. Moreover, the low-boiling substance which exists in the emulsion in its supersaturated (superheated) state is liable to bumping in the case of abrupt pressure change in the living body. This poses a problem with safety.

In addition, the low-boiling substance mentioned above cannot be used to monitor the heat therapy at temperatures exceeding 65° C. The invention disclosed in Patent Document 2 suffers the following disadvantage because it involves emulsification of a substance (such as perfluoropentane) having a boiling point lower than 37° C. at normal pressure with the help of a surfactant (such as lecithin known as phosphatidylcholine). During emulsification, the surfactant forms spherical fine particles called micelle or liposome in water, with water-insoluble matter captured therein. The captured water-insoluble matter is enclosed by the phase of the surfactant in contact with water, so that its molecules are restricted in movement and apparently compressed under the influence of the surfactant. Upon absorption of ultrasonic energy in this state, the phase of the surfactant becomes partly disturbed, causing the apparent pressure of the water-insoluble matter near the disturbed part to decrease to almost normal pressure. This pressure decrease brings about evaporation. Partial evaporation of the water-insoluble matter gradually breaks the phase of the surfactant, eventually leading to entire evaporation. This situation may result in bumping when the ultrasound contrast agent happens to increase in concentration locally in the body to bring about coalescence of bubbles and the water-insoluble matter under the influence of surfactant decreases in concentration.

It is an object of the present invention to provide a highly safe ultrasound contrast agent for ultrasonic molecular imaging and a method for ultrasonography therewith.

Means to Solve Problems

The present invention is based on the investigation by its inventors carried out to develop a safe ultrasound contrast agent which is less liable to bumping and to establish a method for avoiding any situation that will cause bumping. The ultrasound contrast agent according to the present invention is a mixture of a low-boiling water-insoluble substance having a boiling point lower than 37° C. at normal pressure and a high-boiling water-insoluble substance similar to the former in structure having a boiling point higher than 37° C. at normal pressure, the mixture being dispersed into fine particles with the help of a surfactant such as lecithin. When in use, it is exposed to ultrasound under the condition that only the low-boiling water-insoluble substance vaporizes so that the ultrasonic energy absorbed by the low-boiling water-insoluble substance which has vaporized evaporates the high-boiling water-insoluble substance.

The ultrasound contrast agent of the present invention is composed of at least one kind of water-insoluble substance having a boiling point lower than 37° C. at normal pressure (referred to as low-boiling water-insoluble substance) and at least one kind of water-insoluble substance having a boiling point higher than 37° C. at normal pressure (referred to as high-boiling water-insoluble substance). It is administered into a living body in its liquid form, and it vaporizes when it is exposed to ultrasound, thereby producing the imaging effect. Upon exposure to ultrasound, the low-boiling water-insoluble substance vaporizes to absorb ultrasonic energy, thereby resulting in the secondary evaporation of the high-boiling water-insoluble substance. Evaporation of the low- and high-boiling substances takes place upon exposure to ultrasound with a pulse length of 1 to 20 ms. In addition, the ultrasound contrast agent of the present invention also contains a surfactant which is a water-soluble polymer.

The low-boiling water-insoluble substance is any one of straight-chain hydrocarbons, branched-chain hydrocarbons, straight-chain halogenated hydrocarbons, and branched-chain halogenated hydrocarbons. The high-boiling water-insoluble substance is any one of straight-chain hydrocarbons, branched-chain hydrocarbons, straight-chain halogenated hydrocarbons, and branched-chain halogenated hydrocarbons. The former is similar to the latter in structure except that the latter has at least one of its hydrogen atoms or halogen atoms replaced by an alkyl group or halogenated alkyl group, or the latter has at least one of its halogen atoms replaced by a hydrogen atom.

The ultrasound contrast agent of the present invention may be used alone as an ultrasound contrast agent for diagnosis. It may also be used for diagnosis in such a form that its individual particles carry on their surface any one of proteins, antibodies, peptides, and polysaccharides. The additional substance combines with lesions in the living body, thereby allowing for molecular imaging. It may also be used as a contrast agent for MRI or PET if it is chemically or physically combined with a substance capable of image production.

EFFECT OF THE INVENTION

The present invention provides an ultrasound contrast agent for safe diagnosis and therapy.

BEST MODE FOR CARRYING OUT THE INVENTION

The invention will be described in more detail with reference to the following examples, which are not intended to restrict the scope thereof.

The conventional ultrasound contrast agent of single substance vaporizes on the principle illustrated in FIG. 1(a). By contrast, the ultrasound contrast agent of mixed substances according to the example of the present invention vaporizes on the principle illustrated in FIG. 1(b).

As shown in FIG. 1(a), the conventional ultrasound contrast agent of single substance changes in phase from liquid to gas as it absorbs ultrasonic energy. Moreover, it easily undergoes phase change when it receives thermal energy corresponding to ultrasonic energy or pressure fluctuation in the living body. This phase change causes bumping in the living body.

Being a mixture as shown in FIG. 1(b), the ultrasound contrast agent according to the example of the present invention behaves as follows. Upon reception of an ultrasonic energy lasting for about 1 μs and longer, the low-boiling water-insoluble substance (which is a liquid) shown in the left of FIG. 1(b) vaporizes to give a mixed phase of liquid and gas originating from the low-boiling water-insoluble substance, the latter indicated by white circles in the middle of FIG. 1(b). However, the gas evolved in this manner is more dilute than that which is evolved from the ultrasound contrast agent composed of a single substance because of interaction between the gas indicated by white circles and the high-boiling water-insoluble substance surrounding it. This results in discrete minute bubbles. The resulting minute bubbles make their surrounding substance increase in the apparent absorption factor of ultrasonic energy, as described in Non-Patent Document 4. With the increased absorption factor, the high-boiling water-insoluble substance accumulates ultrasonic energy and eventually vaporizes after continued application of ultrasound, as shown in the right of FIG. 1(b). Transformation of the state (liquid-gas phase) shown in the middle of FIG. 1(b) into the state shown in the right of FIG.

1(b) stops when application of ultrasound is suspended. It is completed when application of ultrasound is continued for 1 to 20 ms (say, about 5 ms). It is to be noted that the high-boiling water-insoluble substance is evaporated not by the energy of applied ultrasound but by the energy of ultrasound accumulated in bubbles (or vapor) originating from the low-boiling water-insoluble substance. This means that the high-boiling water-insoluble substance will not be able to acquire energy necessary for its evaporation from the changing temperature or pressure in the living body. These difficulties are overcome by the ultrasound contrast agent according to the example of the present invention, which permits transformation from liquid to gas to take place under mild conditions only in legions to which ultrasound is applied.

The ultrasound contrast agent of the present invention may also be composed of more than one low-boiling water-insoluble substances and more than one high-boiling water-insoluble substances. In this case, too, the constituent substances are sequentially evaporated according to their boiling points upon application of pulsed ultrasound. Thus, transformation from liquid to gas takes place as shown in the left of FIG. 1(b) in the same way as mentioned above.

The low-boiling water-insoluble substance used in the example of the present invention is one which is highly biocompatible and liquid at the time of administration, as disclosed in Patent Document 2. It is not specifically restricted so long as it has a boiling point lower than about 37° C. under normal pressure. More than one such substance may be used depending on the method for application of ultrasound. With ultrasound properly controlled in pulse length, it allows for imaging even when time required for imaging is limited by the size and kind of lesions.

Some of the low-boiling water-insoluble substance used in the example of the present invention and their boiling points under normal pressure are listed in FIG. 2. They are hydrocarbons with 1 to 5 carbon atoms.

Some of the high-boiling water-insoluble substance used in the example of the present invention and their boiling points under normal pressure are listed in FIG. 3. They are hydrocarbons with 5 to 8 carbon atoms.

Of the low-boiling water-insoluble substances, fluorinated hydrocarbons are preferable because of their strong interaction with the high-boiling water-insoluble substances through fluorine atoms.

The ultrasound contrast agent of the present invention may be composed of more than one each of low-boiling water-insoluble substance and high-boiling water-insoluble substance. It permits imaging by application of pulsed ultrasound for a controlled length of time even if time required for imaging is restricted by the size and kind of lesions. In other words, it permits imaging in a short time or long time under different circumstances.

The high-boiling water-insoluble substance used in the example of the present invention should be one which is similar in chemical structure to the low-boiling water-insoluble substance so that the two substances are highly miscible and reactive with each other. For this reason, the high-boiling water-insoluble substance should have such a structure that the low-boiling water-insoluble substance has a hydrophobic functional group such as alkyl group and fluorinated alkyl group or the low-boiling water-insoluble substance has its fluorine atoms partly replaced by hydrogen.

In addition, the high-boiling water-insoluble substance used in the example of the present invention may be incorporated with a stabilizer that helps the high-boiling water-insoluble substance to vaporize as the vaporized low-boiling water-insoluble substance absorbs ultrasound energy and also helps the vaporized component to become minute particles. A preferable stabilizer is any substance which is highly reactive with both the low-boiling water-insoluble substance and the high-boiling water-insoluble substance. It may also contain a water-insoluble polymer.

The ultrasound contrast agent of the present invention may also contain a surfactant which encloses the mixture of the low-boiling water-insoluble substance and the high-boiling water-insoluble substance. The surfactant is not specifically restricted so long as it is a highly biocompatible one, as disclosed in Patent Document 2. Lecithin is preferable because of its high biocompatibility. The surfactant may have its structure partly modified with a carboxylic acid halide or SH group.

The ultrasound contrast agent of the present invention may be used alone or in combination with a molecular probe chemically or physically attached thereto. The molecular probe may be selected from antibodies (monoclonal and polyclonal), enzymes, biotin, proteins (streptavidin), nucleic acids (DNA and RNA), and peptides. For diagnosis of tumor, peptides and antibodies are preferable as mentioned in Non-Patent Document 1.

The ultrasound contrast agent to be used alone may be incorporated with a water-soluble polymer (such as polyethylene glycol) that encloses the emulsified particles so as to prevent them from being absorbed by the liver's reticular system (which serves to capture fine particles administered into the living body).

The ultrasound contrast agents demonstrated in the following examples contain glycerin as a viscosity adjusting agent, α-tocopherol as an antioxidant, cholesterol as a stabilizer, and lecithin as a surfactant.

EXAMPLE 1

Ultrasound Contrast Agent in the Form of Microemulsion of a Mixture of Perfluoropentane and Perfluoroheptane In the first step, an emulsion was prepared from the following ingredients by homogenizing them with 20 mL of distilled water (which was slowly added) for 1 minute in a homogenizer running at 9500 rpm with ice cooling. (The homogenizer is ULTRA-TURRAX T25 from Janke & Knukel, Staufen, Germany).

| | |
|---|---|
| Glycerin | 2.0 g |
| α-tocopherol | 0.02 g |
| Cholesterol | 0.1 g |
| Lecithin | 1.0 g |
| Perfluoropentane | N g |
| Perfluoroheptane | (0.2 − N) g |

(where N is 0 to 0.2, and hence the amount of perfluoroheptane is 0 to 0.2 g.)

In the second step, the resulting emulsion was further emulsified at 20 MPa for 2 minutes in a high-pressure emulsifier (Emulsiflex-C5, from Avestin, Ottawa Canada). The resulting product was filtered through a membrane filter (0.4 μm). Thus there was obtained a sample of nearly transparent microemulsion.

The microemulsion was found to be composed of fine particles (accounting for more than 98%) having a diameter smaller than 200 nm. The particle diameter was measured by using an apparatus for measuring the particle size distribution by dynamic light scattering (Model LB-550, from Horiba Ltd, Tokyo). Incidentally, the step of high-pressure emulsification may be omitted if the object emulsion needs a particle diameter larger than 200 nm.

The microemulsion of the ultrasound contrast agent prepared in this example has a particle size distribution as shown in FIG. 4. It is noted from FIG. 4 that the microemulsion has particle diameters ranging from 0.025 μm to 0.25 μm, with the median diameter being 0.07 μm. The resulting sample of microemulsion was tested for phase change from liquid to gas. The method and result of the test are shown in FIGS. 5 and 6.

The test was conducted by using an apparatus shown in FIG. 5, which is designed for imaging by application of ultrasound to the sample of the ultrasound contrast agent.

The test procedure is as follows. The water bath 1 is filled with degassed water 2 (at 37° C.). The vinyl tube 6 (2 mm in inside diameter) filled with the ultrasound contrast agent (microemulsion) 5 is attached to the holder 3-1 by means of the clamps 4-1 and 4-2. The ultrasound transducer 7 and the diagnostic probe 11 are attached to the holder 3-2. The ultrasound transducer 7, which is driven by the waveform generator 8 and the amplifier 9, applies pulsed ultrasound, 3 MHz (5 ms ON and 55 ms OFF), for 1 s. During application of ultrasound, the diagnostic probe 11, which is connected to the ultrasound diagnostic unit 10, acquires the ultrasound image from the ultrasound contrast agent 5. Incidentally, the ultrasound diagnostic unit is EUB-8500 and the diagnostic probe 11 is EUP-53 (7.5 MHz), both from Hitachi Medico.

When the intensity of ultrasound applied to the ultrasound contrast agent gradually increases and reaches a threshold value, brightness suddenly changes in the ultrasound diagnostic unit and bumping occurs in the ultrasound contrast agent. This is illustrated in FIG. 6.

The abscissa of FIG. 6 represents the concentration of perfluoropentane relative to the total amount of perfluoropentane and perfluoroheptane constituting the ultrasound contrast agent. The ordinate of FIG. 6 represents the threshold intensity of ultrasound which is high enough for brightness to change in the ultrasound diagnostic unit and bumping to occur in the ultrasound contrast agent. Change in brightness is due to the occurrence of microbubbles of the order of microns, and bumping is due to the occurrence of large bubbles of the order of millimeters. The threshold intensity of ultrasound for bumping was obtained by noticing the occurrence of large bubbles in the image.

The same results as shown in FIG. 6 were obtained when ultrasound from the ultrasound transducer was applied under different conditions (1 ms ON and 59 ms OFF, 10 ms ON and 40 ms OFF, and 20 ms ON and 50 ms OFF). The threshold intensity of ultrasound that changes brightness tends to increase as the relative concentration of perfluoropentane decreases. The threshold intensity of ultrasound that causes bumping remains almost constant so long as the ultrasound contrast agent is composed of perfluoropentane and perfluoroheptane (or except when the relative concentration of perfluoropentane is 0 or 1). The threshold intensity in the case of mixture is twice as large as that in the case of perfluoroheptane used alone.

The foregoing results suggest that the ultrasound contrast agent having a relative concentration of perfluoropentane ranging from about 0.6 to 0.9 has a threshold intensity of ultrasound that causes bumping which is twice that of the ultrasound contrast agent containing perfluoroheptane alone. This increased threshold value is attained without appreciable change in the threshold intensity of ultrasound that changes brightness.

FIG. 6 suggests that the ultrasound contrast agent of the present invention (which is composed of a low-boiling water-insoluble substance and a high-boiling water-insoluble substance) will produce varied brightness in the ultrasound diagnostic image without causing bumping in the living body if it contains perfluoropentane in a relative concentration lower than about 0.6. In other words, it evidently produces its effect due to phase change from liquid to gas.

The ultrasound contrast agent of the present invention has a threshold temperature at which its brightness changes in the diagnostic image when it is gradually heated. This is illustrated in FIG. 7.

As in FIG. 6, FIG. 7 is based on an experiment with the ultrasound contrast agent containing perfluoropentane and perfluoroheptane. The experiment was carried out by using the same apparatus as shown in FIG. 5 in such a way that the deaerated water 2 was varied in temperature, with the output from the ultrasound transducer 7 kept zero. The threshold temperature at which brightness changes in the image from the diagnostic probe 11 is plotted against the concentration of perfluoropentane relative to the total amount of perfluoropentane and perfluoroheptane.

It is noted from FIG. 7 that the threshold temperature at which brightness changes evidently decreases as the relative concentration of perfluoropentane increases. This suggests that the ultrasound contrast agent will produce bubbles at any temperature between 30° C. and 80° C. if it contains perfluoropentane and perfluoroheptane in a proper ratio.

FIG. 7 indicates that the ultrasound contrast agent containing perfluoroheptane in a relative concentration of about 0.2 vaporizes to evolve bubbles detectable on the monitor when the temperature reaches 65° C. This suggests that the ultrasound contrast agent can be used as a temperature monitoring drug that tells whether or not the temperature has reached 65° C. at the specific position in a living body into which it has been introduced. Such temperature sensitiveness is important for therapy involving protein coagulation that occurs at 65° C. and above as in the case of ultrasonic or RF heating and coagulation. FIG. 7 also suggests that an ultrasound contrast agent containing perfluoroheptane in a relative concentration of 0.4 will be used as a temperature monitoring drug which vaporizes at 55° C. It will be useful for monitoring at lower temperatures in the case where a heat-sensitive part exists near a lesion to be cured, heating under milder conditions than usual is necessary, or heating takes place too fast to control by feedback. The relation between the threshold temperature and the relative concentration of perfluoroheptane as shown in FIG. 7 may be utilized to prepare an ultrasound contrast agent having an adequate composition suitable for the temperature to be monitored. The resulting ultrasound contrast agent will be used to monitor temperatures in therapy by ultrasonic heating or RF heating. The foregoing demonstrates that the ultrasound contrast agent according to the present invention produces the effect of monitoring temperatures.

The same effect as in this example were produced when the low-boiling water-insoluble substance and the high-boiling water-insoluble substance are respectively perfluoropentane and perfluoroheptane, perfluoropentane and 2H,6H-perfluoropentane, isopentane and hexane, or isopentane and heptane.

EXAMPLE 2

Ultrasound Contrast Agent of Microemulsion Composed of Perfluoropentane and 2H,3H-Perfluoropentane In the first step, an emulsion was prepared from the following ingredients by homogenizing them with 20 mL of distilled water (which was slowly added) for 1 minute in a homogenizer running at 9500 rpm with ice cooling. (The homogenizer is ULTRA-TURRAX T25 from Janke & Knukel, Staufen, Germany).

| | |
|---|---|
| Glycerin | 2.0 g |
| α-tocopherol | 0.02 g |
| Cholesterol | 0.1 g |
| Lecithin | 1.0 g |
| Perfluoropentane | N g |
| 2H,3H-perfluoroheptane | (0.2 − N) g |

(where N is 0 to 0.2, and hence the amount of 2H,3H-perfluoroheptane is 0 to 0.2 g.)

In the second step, the resulting emulsion was further emulsified at 20 MPa for 2 minutes in a high-pressure emulsifier (Emulsiflex-C5, from Avestin, Ottawa Canada). The resulting product was filtered through a membrane filter (0.4 μm). Thus there was obtained a sample of nearly transparent microemulsion.

The microemulsion was found to be composed of fine particles (accounting for more than 98%) having a diameter smaller than 200 nm. The particle diameter was measured by using an apparatus for measuring the particle size distribution by dynamic light scattering (Model LB-550, from Horiba Seisakusho, Tokyo).

EXAMPLE 3

Ultrasound Contrast Agent of Microemulsion Composed of Isopentane and Hexane

In the first step, an emulsion was prepared from the following ingredients by homogenizing them with 20 mL of distilled water (which was slowly added) for 1 minute in a homogenizer running at 9500 rpm with ice cooling. (The homogenizer is ULTRA-TURRAX T25 from Janke & Knukel, Staufen, Germany).

| | |
|---|---|
| Glycerin | 2.0 g |
| α-tocopherol | 0.02 g |
| Cholesterol | 0.1 g |
| Lecithin | 1.0 g |
| Isopentane | N g |
| Hexane | (0.2 − N) g |

(where N is 0 to 0.2, and hence the amount of hexane is 0 to 0.2 g.)

In the second step, the resulting emulsion was further emulsified at 20 MPa for 2 minutes in a high-pressure emulsifier (Emulsiflex-C5, from Avestin, Ottawa Canada). The resulting product was filtered through a membrane filter (0.4 μm). Thus there was obtained a sample of nearly transparent microemulsion.

The microemulsion was found to be composed of fine particles (accounting for more than 98%) having a diameter smaller than 200 nm. The particle diameter was measured by using an apparatus for measuring the particle size distribution by dynamic light scattering (Model LB-550, from Horiba Ltd, Tokyo).

EXAMPLE 4

Ultrasound Contrast Agent of Microemulsion Composed of Perfluoropentane and Perfluorohexane with Polymer Coating In the first step, an emulsion was prepared from the following ingredients by homogenizing them with 20 mL of distilled water (which was slowly added) for 1 minute in a homogenizer running at 9500 rpm with ice cooling. (The homogenizer is ULTRA-TURRAX T25 from Janke & Knukel, Staufen, Germany).

| | |
|---|---|
| mPEG-2000-PE(*) | 0.05 g |
| Glycerin | 2.0 g |
| α-tocopherol | 0.02 g |
| Cholesterol | 0.1 g |
| Lecithin | 1.0 g |
| Perfluoropentane | N g |
| Perfluorohexane | (0.2 − N) g |

(where N is 0 to 0.2, and hence the amount of perfluorohexane is 0 to 0.2 g.)

(*)Abbreviation of 1,2-Diacyl-sn-Glycero-3-Phosphoethanolamine-N-[Methoxy(Polyethylene glycol)-2000], available from Avanti (Alabama, USA), catalog No. 880160.

In the second step, the resulting emulsion was further emulsified at 20 MPa for 2 minutes in a high-pressure emulsifier (Emulsiflex-C5, from Avestin, Ottawa Canada). The resulting product was filtered through a membrane filter (0.4 μm). Thus there was obtained a sample of nearly transparent microemulsion.

The microemulsion was found to be composed of fine particles (accounting for more than 98%) having a diameter smaller than 200 nm. The particle diameter was measured by using an apparatus for measuring the particle size distribution by dynamic light scattering (Model LB-550, from Horiba Seisakusho, Tokyo).

The procedure in Example 4 was repeated except that mPEG-2000-PE was replaced by 1,2-Distearoyl-sn-Glycero-3-Phosphoethanolamine-N-[Biotinyl(polyethylene Glycol)-2000. There was obtained an ultrasound contrast agent which has biotin (as a molecular probe) chemically attached thereto.

The ultrasound contrast agent mentioned above will be used for ultrasonography in the following way according to the present invention.

The method for ultrasonography comprises a step of injecting into a vein of a living body the ultrasonic contrast agent which is liquid at the time of injection and composed of least one kind of low-boiling water-insoluble substance (with a boiling point lower than 37° C.) and at least one kind of high-boiling water-insoluble substance (with a boiling point higher than 37° C.), and a step of applying pulsed ultrasound to evaporate said low- and high-boiling water-insoluble substances.

The method for ultrasonography mentioned above is characterized in that the application of pulsed ultrasound to a living body lasts for 1 ms to 20 ms.

The ultrasound contrast agent according to the present invention may also be used as a temperature monitoring drug as explained in the following.

(1) The ultrasound contrast agent used as a temperature monitoring drug in the form of liquid at the time of injection into a vein of a living body, which is composed of a low-boiling water-insoluble substance (with a boiling point lower than 37° C.) and a high-boiling water-insoluble substance (with a boiling point higher than 37° C.), said two substances being mixed in a varied ratio such that they evolve bubbles in the living body at a specific temperature which is associated with the occurrence of bubbles.

(2) The ultrasound contrast agent used as a temperature monitoring drug mentioned in (1) above, in which the low-boiling water-insoluble substance is any one of straight-chain hydrocarbons, branched-chain hydrocarbons, straight-chain halogenated hydrocarbons, and branched-chain halogenated hydrocarbons.

(3) The ultrasound contrast agent used as a temperature monitoring drug mentioned in (1) above, in which the high-boiling water-insoluble substance is any one of straight-chain hydrocarbons, branched-chain hydrocarbons, straight-chain halogenated hydrocarbons, and branched-chain halogenated hydrocarbons.

(4) The ultrasound contrast agent used as a temperature monitoring drug mentioned in (1) above, in which the high-boiling water-insoluble substance has the same structure as the low-boiling water-insoluble substance except that it has its one hydrogen atom or halogen atom replaced by an alkyl group or halogenated alkyl group.

(5) The ultrasound contrast agent used as a temperature monitoring drug mentioned in (1) above, in which the high-boiling water-insoluble substance has the same structure as the low-boiling water-insoluble substance except that it has its one halogen atom replaced by a hydrogen atom.

(6) The ultrasound contrast agent used as a temperature monitoring drug mentioned in (1) above, which contains a surfactant.

(7) The ultrasound contrast agent used as a temperature monitoring drug mentioned in (6) above, in which the surfactant has a structure containing a water-soluble polymer.

(8) The ultrasound contrast agent used as a temperature monitoring drug mentioned in (7) above, in which the water-soluble polymer contains polyethylene glycol.

EXAMPLE 5

Although the ultrasound contrast agents according to Examples 1 to 4 mentioned above are designed on the assumption that they will receive ultrasound with an intensity of 0.1 to 20 W/cm$^2$ (SPTA) and they will vaporize upon application of ultrasound with a pulse length of 1 ms to 20 ms, they are modified in this example so that they vaporize upon application of ultrasound with a pulse length longer than 1 μs when the intensity of ultrasound exceeds 20 W/cm$^2$. In this case, however, ultrasound should have a pulse length shorter than 1 ms to prevent bumping. The ultrasound contrast agent in Example 1, which is illustrated in FIG. 6, changes in brightness at any pulse length of 1 μs ON/20 ms OFF, 10 μs ON/20 ms OFF, or 20 ms ON/50 ms OFF, regardless of the relative concentration of perfluoropentane when the intensity of ultrasound from the transducer 7 is higher than 20 W/cm$^2$.

Exploitation in Industry

The present invention provides an ultrasound contrast agent which is less liable to bumping in a living body and hence safe and is useful for diagnosis and therapy by selective imaging of lesions.

BRIEF DESCRIPTION OF THE DRAWINGS

FIG. 1 is a schematic diagram illustrating the principle on which the ultrasound contrast agent of the present invention vaporizes.

FIG. 2 shows some of the low-boiling water-insoluble substance preferably used in the example of the present invention and their boiling points under normal pressure.

FIG. 3 shows some of the high-boiling water-insoluble substance preferably used in the example of the present invention and their boiling points under normal pressure.

Explanation of Letters or Numerals

Figure 4:
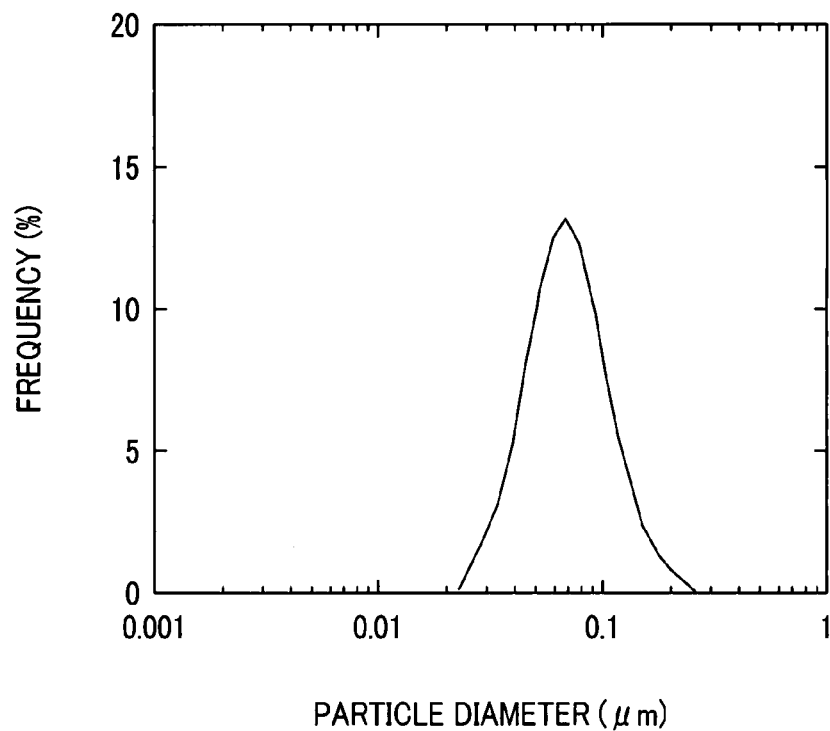
FIG. 4 shows the particle size distribution of the ultrasound contrast agent according to the example of the present invention.
Figure 5:
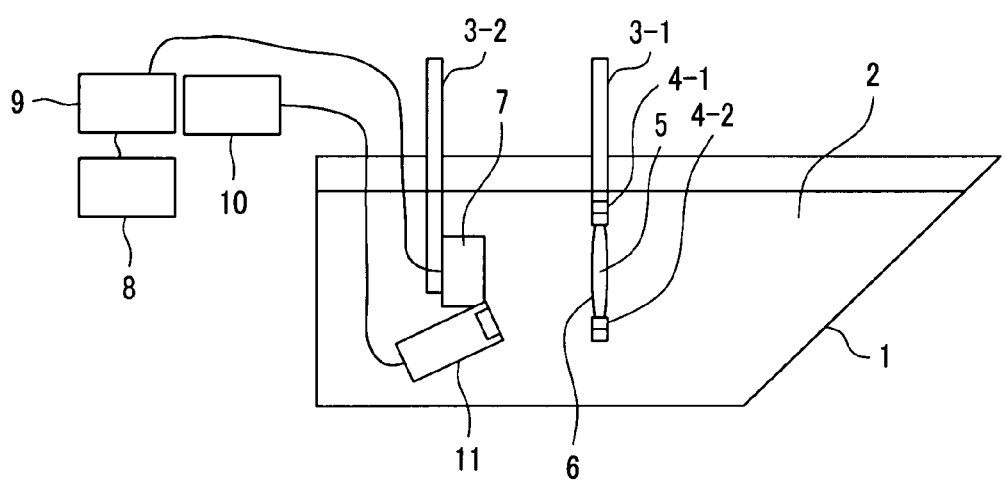
FIG. 5 shows an experimental apparatus for ultrasonography with the ultrasound contrast agent according to the example of the present invention.
Figure 6:
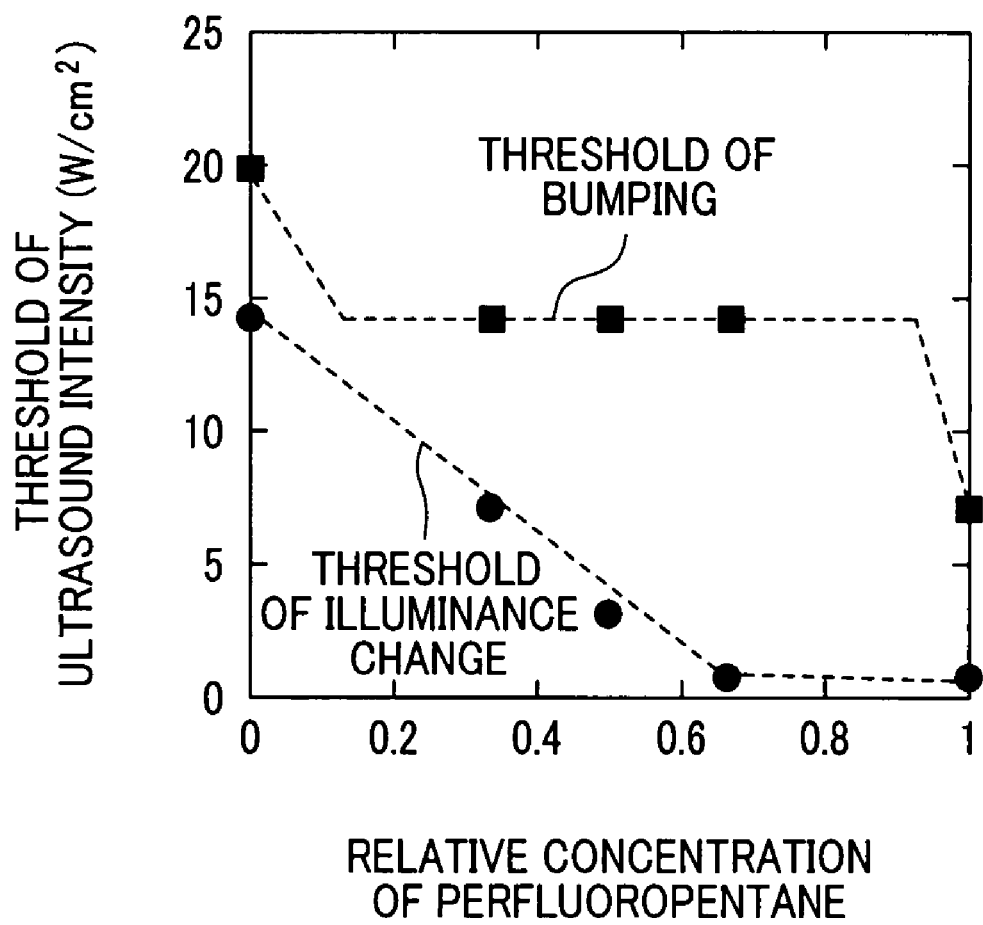
FIG. 6 shows the threshold intensity of ultrasound at which the ultrasound contrast agent of the present invention suddenly changes in brightness on the monitor and suffers bumping when the intensity of ultrasound gradually increases.
Figure 7:
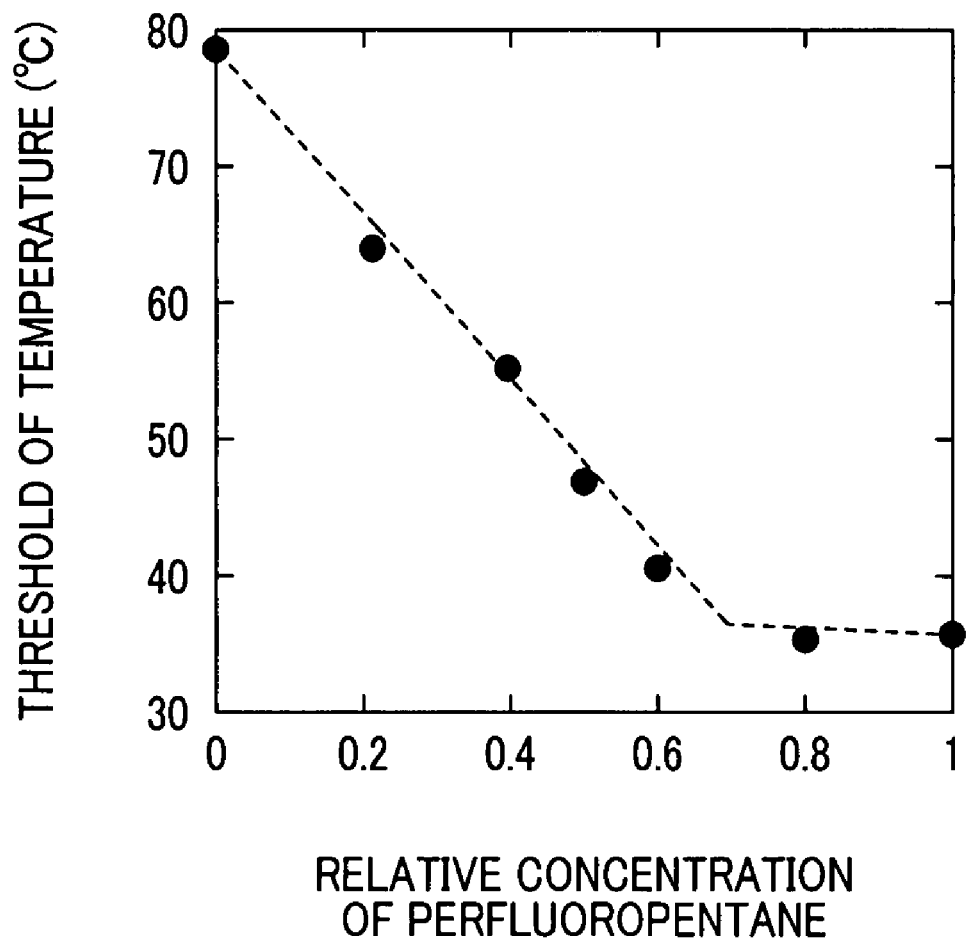
FIG. 7 shows the threshold temperature at which the ultrasound contrast agent of the present invention suddenly changes in brightness on the monitor when it is gradually heated.

1: water bath, 2: deaerated water, 3-1 and 3-2: holders, 4-1 and 4-2: clamps, 5: ultrasonic contrast agent, 6: vinyl tube, 7: ultrasound transducer, 8: waveform generator, 9: amplifier, 10: ultrasonographic equipment, and 11: diagnostic probe.

The invention claimed is:

1. An ultrasound contrast agent in the form of particles, comprising:
 a perfluoropentane as a low-boiling point water-insoluble substance; and
 a perfluoroheptane as a high-boiling point water-insoluble substance; wherein a relative concentration of the perfluoropentane to the total amount of the perfluoropentane and the perfluoroheptane is lower than 0.7, and the ultrasound contrast agent is a liquid at the time of administration into a living body, and wherein the low-boiling point water-insoluble substance is directly vaporized by an application of pulsed ultrasound with a pulse length of 1 ms to 20 ms, and the high-boiling point water-insoluble substance is indirectly vaporized by the ultrasound by being vaporized by the low-boiling point water-insoluble vapor, so that vaporization of the low-boiling point water-insoluble substance and the high-boiling point water-insoluble substance is used to give an image.

2. The ultrasound contrast agent according to claim 1, wherein the relative concentration of the perfluoropentane to the total amount of the perfluoropentane and the perfluoroheptane is lower than 0.2.

3. The ultrasound contrast agent according to claim 1, wherein the relative concentration of the perfluoropentane to the total amount of the perfluoropentane and the perfluoroheptane is about 0.4.

4. The ultrasound contrast agent according to claim 1, which further comprises a surfactant.

5. The ultrasound contrast agent according to claim 4, wherein the surfactant has a structure which contains a water-soluble polymer.

6. The ultrasound contrast agent according to claim 5, wherein the water-soluble polymer contains polyethylene glycol.

7. The ultrasound contrast agent according to claim 1, wherein the particles of the contrast agent carry on the surface thereof proteins, antibodies, peptides, or polysaccharides attached thereto.

8. The ultrasound contrast agent according to claim 1, wherein the pulsed ultrasound has an intensity of 0.1 to 20 W/cm$^2$.

9. The ultrasound contrast agent according to claim 1, wherein the water-insoluble substances vaporize upon application of pulsed ultrasound with an intensity higher than 20 W/cm$^2$.

10. A method for producing an ultrasound image, comprising the steps of:
 providing an ultrasound contrast agent of claim 1,
 administering said ultrasound contrast agent in a liquid phase into a living body,
 applying a pulsed ultrasound having a pulse length in a range of 1 ms to 20 ms to a portion of said living body,
 vaporizing at least a portion of said low-boiling point water-insoluble substance directly by application of said pulsed ultrasound to said portion of said living body whereby the vaporized low-boiling point water-insoluble substance vaporizes the high-boiling point water-insoluble substance, and
 producing an ultrasound image.

* * * * *